US008153830B2

(12) United States Patent
Hirata et al.

(10) Patent No.: US 8,153,830 B2
(45) Date of Patent: Apr. 10, 2012

(54) PRODUCTION METHOD OF ASYMMETRIC COPPER COMPLEX CRYSTAL

(75) Inventors: Norihiko Hirata, Suita (JP); Takanori Yoshimiya, Ibaraki (JP); Yoshihiko Iwanaga, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 313 days.

(21) Appl. No.: 12/444,690

(22) PCT Filed: Oct. 11, 2007

(86) PCT No.: PCT/JP2007/070304
§ 371 (c)(1),
(2), (4) Date: Apr. 8, 2009

(87) PCT Pub. No.: WO2008/050661
PCT Pub. Date: May 2, 2008

(65) Prior Publication Data
US 2010/0094036 A1 Apr. 15, 2010

(30) Foreign Application Priority Data

Oct. 26, 2006 (JP) ................................. 2006-290993

(51) Int. Cl.
*C07F 15/06* (2006.01)
(52) U.S. Cl. ........................................................ 556/32
(58) Field of Classification Search ...................... 556/32
See application file for complete search history.

(56) References Cited

U.S. PATENT DOCUMENTS

| 4,029,683 | A * | 6/1977 | Aratani et al. .................... 556/32 |
| 2001/0037036 | A1 * | 11/2001 | Suzukamo et al. ............. 560/124 |
| 2003/0233003 | A1 * | 12/2003 | Itagaki et al. .................... 556/32 |
| 2006/0211879 | A1 * | 9/2006 | Itagaki .......................... 560/124 |
| 2007/0099886 | A1 * | 5/2007 | Gupta ............................ 514/184 |
| 2011/0166372 | A1 * | 7/2011 | Masumoto et al. ............. 556/32 |

FOREIGN PATENT DOCUMENTS

| JP | 5024254 A | 3/1975 |
| JP | 2000247934 A | 9/2000 |
| JP | 2001278853 A | 10/2001 |
| JP | 2002241356 A | 8/2002 |
| JP | 2003096036 A | 4/2003 |
| JP | 2004018379 A | 1/2004 |

OTHER PUBLICATIONS

Itagaki. M. et al.: Highly Efficient Chiral Copper Schiff-Base Catalyst for Asymmetric Cyclopropanation of 2,5-dimethyl-2, 4-hexadiene, Tetrahedron, vol. 60, pp. 7835-7843 (2004).
Zhengning, Li et al.: Asymmetric Cyclopropanation of Styrene Catalyzed by Cu-(Chiral Schiff-Base) Complexes, Tetrahedron, vol. 56, pp. 7187-7191 (2000).
Zhengning, Li et al.: Asymmetric Cyclopropanation Catalyzed by Copper-Schiff's Base Complexes, Journal of Molecular Catalysis A: Chemical, vol. 165, pp. 67-71 (2001).
Ohga, T. et al.: Enantioselective Addition of Diethylzinc to Aldeydes Catalyzed by Chiral Amino Alcohols. Substituent Effect and Nonlinear Effect, Tetrahedron, vol. 57, pp. 4825-4829 (2001).
Hintermann, T. et al.: A Useful Modification of the Evans Auxiliary: 4-Isopropyl-5, 5-Diphenyloxazolidin-2-One, Helvetica Chemica Acta, vol. 81, pp. 2093-2126 (1998).

* cited by examiner

*Primary Examiner* — Porfirio Nazario Gonzalez
(74) *Attorney, Agent, or Firm* — Panitch Schwarze Belisario & Nadel LLP

(57) ABSTRACT

A method of producing an asymmetric copper complex crystal comprising reacting an optically active salicylidene amino alcohol compound with a copper compound, then, performing a crystallization treatment in the presence of an alcohol solvent.

16 Claims, No Drawings

PRODUCTION METHOD OF ASYMMETRIC COPPER COMPLEX CRYSTAL

CROSS-REFERENCE TO RELATED APPLICATION

This application is a section 371 of International Application No. PCT/JP2007/070304, filed Oct. 11, 2007, which was published in the Japanese language on May 2, 2008 under International Publication No. WO 2008/050661 A1 and the disclosure of which is incorporated herein by reference.

TECHNICAL FIELD

The present invention relates to a method of producing an asymmetric copper complex crystal.

BACKGROUND ART

An asymmetric copper complex obtained by reacting an optically active salicylidene amino alcohol compound with a copper compound is useful as a catalyst for asymmetric synthesis using a diazo compound, or the like (see, patent document 1). As a method for getting out such an asymmetric copper complex in the form of crystal, there is known a method of performing a crystallization treatment in the presence of an aliphatic hydrocarbon after the complexation reaction (see, patent document 2).

[patent document 1] JP-A No. 50-24254
[patent document 2] JP-A No. 2002-241356

DISCLOSURE OF THE INVENTION

It has been found, however, that in the case of inclusion of impurities in an optically active salicylidene amino alcohol compound in the method of producing such an asymmetric copper complex crystal, even if a crystallization treatment is carried out in the presence of an aliphatic hydrocarbon, it is difficult to obtain an asymmetric copper complex crystal with good purity.

The present inventors have investigated a method of producing an asymmetric copper complex crystal and resultantly found that an asymmetric copper complex crystal is obtained with good purity even if an optically active salicylidene amino alcohol compound containing impurities is used, by performing a crystallization treatment in the presence of an alcohol solvent after carrying out a complexation reaction.

That is, the present invention provides the following [1] to [20].

[1]. A method of producing an asymmetric copper complex crystal comprising reacting an optically active salicylidene amino alcohol compound of the formula (1):

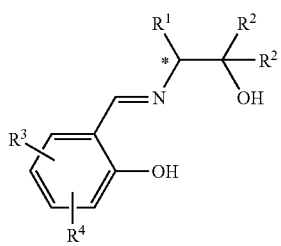

(1)

(wherein, $R^1$ represents an alkyl group, aryl group or aralkyl group, $R^2$ represents an optionally substituted alkyl group or optionally substituted phenyl group, $R^3$ and $R^4$ are the same or mutually different and represent a hydrogen atom, halogen atom, nitro group, alkyl group, fluoroalkyl group, alkoxy group, alkoxycarbonyl group, trialkylsilyl group or cyano group, and * represents that the carbon atom is an optically active point.)
with a copper compound, then, performing a crystallization treatment in the presence of an alcohol solvent.

[2]. The production method according to [1], wherein the alcohol solvent is methanol.

[3]. The production method according to [1] or [2], wherein the copper compound is a divalent copper compound.

[4]. The production method according to [3], wherein the divalent copper compound is copper(II) acetate or copper(II) hydroxide.

[5]. The production method according to [3], wherein the divalent copper compound is copper(II) acetate.

[6]. The production method according to any one of [1] to [5], wherein the optically active salicylidene amino alcohol compound of the formula (1) is a compound obtained by reacting an optically active amino alcohol

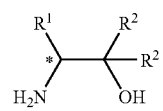

(2)

compound of the formula (2):
(wherein, $R^1$, $R^2$ and * represent the same meanings as described above.)
with a salicylaldehyde compound of the formula (3):

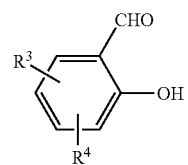

(3)

(wherein, $R^3$ and $R^4$ represent the same meanings as described above.).

[7]. The production method according to [6], wherein the optically active amino alcohol compound of the formula (2) is a compound obtained by reacting an optically active amino acid ester compound of the formula (4):

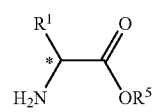

(4)

(wherein, $R^1$ and * represent the same meanings as described above, and $R^5$ represents an optionally substituted alkyl group or optionally substituted phenyl group.)
with a Grignard compound of the formula (5):

$$R^2\text{—MgX} \quad (5)$$

(wherein, $R^2$ represents the same meaning as described above, and X represents a halogen atom.).

[8]. The production method according to [7], wherein X in the formula (5) is a bromine atom.

[9]. The production method according to [7], wherein the optically active amino acid ester compound of the formula (4) is a compound obtained by treating an addition salt of the optically active amino acid ester compound and an acid with a base.

[10]. The production method according to [9], wherein the base is a tertiary amine compound.

[11]. The production method according to [10], wherein the tertiary amine compound is triethylamine.

[12]. The production method according to any one of [9] to [11], wherein the acid is an organic sulfonic acid compound.

[13]. The production method according to [12], wherein the organic sulfonic acid compound is p-toluenesulfonic acid.

[14]. The production method according to any one of [9] to [13], wherein the temperature for treatment of an addition salt of the optically active amino acid ester compound of the formula (4) and an acid with a base is in the range of 0 to 10° C.

[15]. The production method according to any one of [1] to [14], wherein $R^1$ in the formula (1) is an alkyl group having 1 to 4 carbon atoms.

[16]. The production method according to any one of [1] to [14], wherein $R^1$ in the formula (1) is a methyl group.

[17]. The production method according to any one of [1] to [16], wherein $R^2$ in the formula (1) is an optionally substituted phenyl group.

[18]. The production method according to any one of [1] to [16], wherein $R^2$ in the formula (1) is a 2-n-butoxy-5-tert-butylphenyl group.

[19]. The production method according to any one of [1] to [18], wherein $R^3$ is a hydrogen atom and $R^4$ is a nitro group in the formula (1).

[20]. The production method according to [19], wherein the nitro group represented by $R^4$ in the formula (1) is linked to the 5-position on the connected phenyl group.

MODES FOR CARRYING OUT THE INVENTION

The present invention will be illustrated in detail below.

Examples of the alkyl group represented by $R^1$ in the optically active salicylidene amino alcohol compound of the above-described formula (1) (hereinafter, abbreviated as salicylidene amino alcohol compound (1)) include alkyl groups having 1 to 4 carbon atoms such as a methyl group, ethyl group, n-propyl group, isopropyl group, n-butyl group, isobutyl group, sec-butyl group, tert-butyl group and the like. Examples of the aryl group include a phenyl group, naphthyl group and the like. Examples of the aralkyl group include a benzyl group, trityl group and the like. $R^1$ is preferably an alkyl group having 1 to 4 carbon atoms, more preferably a methyl group.

Examples of the alkyl group represented by $R^2$ include alkyl groups having 1 to 4 carbon atoms such as a methyl group, ethyl group, n-propyl group, isopropyl group, n-butyl group, tert-butyl group and the like. Such an alkyl group is optionally substituted by, for example, an alkoxy group such as a methoxy group, ethoxy group, propoxy group, isopropoxy group and the like, or a phenyl group and the like, and specific examples of the alkyl group substituted by such a substituent include a methoxymethyl group, ethoxymethyl group, methoxyethyl group, benzyl group, trityl group and the like.

Examples of the substituent optionally substituted on a phenyl group represented by $R^2$ include alkyl groups having 1 to 4 carbon atoms such as a methyl group, ethyl group, n-propyl group, isopropyl group, n-butyl group, isobutyl group, sec-butyl group, tert-butyl group and the like; alkoxy groups having 1 to 10 carbon atoms such as a methoxy group, ethoxy group, n-propoxy group, isopropoxy group, n-butoxy group, isobutoxy group, sec-butoxy group, tert-butoxy group, n-pentyloxy group, n-hexyloxy group, n-octyloxy group, isooctyloxy group, n-decyloxy group and the like; and the like. Specific examples of the phenyl group substituted by such a substituent include a 2-methoxyphenyl group, 2-n-butoxy-5-tert-butylphenyl group, 2-tert-butoxy-5-tert-butylphenyl group, 2-n-octyloxy-5-tert-butylphenyl group and the like.

$R^2$ is preferably an optionally substituted phenyl group, more preferably a 2-n-butoxy-5-tert-butylphenyl group.

Examples of the halogen atom represented by $R^3$ and $R^4$ include a fluorine atom, chlorine atom, bromine atom and the like. Examples of the alkyl group include alkyl groups having 1 to 4 carbon atoms such as a methyl group, ethyl group, n-propyl group, isopropyl group, n-butyl group, isobutyl group, sec-butyl group, tert-butyl group and the like. Examples of the fluoroalkyl group include groups obtained by substituting one or more hydrogen atoms constituting alkyl groups having 1 to 4 carbon atoms by a fluorine atom such as a fluoromethyl group, trifluoromethyl group, fluoroethyl group, 2,2,2-trifluoroethyl group, pentafluoroethyl group, nonafluorobutyl group and the like. Examples of the alkoxy group include alkoxy groups having 1 to 10 carbon atoms such as a methoxy group, ethoxy group, n-propoxy group, isopropoxy group, n-butoxy group, isobutoxy group, sec-butoxy group, tert-butoxy group, n-pentyloxy group, n-hexyloxy group, n-octyloxy group, isooctyloxy group, n-decyloxy group and the like. Examples of the alkoxycarbonyl group include alkoxycarbonyl groups having 2 to 5 carbon atoms such as a methoxycarbonyl group, ethoxycarbonyl group, n-propoxycarbonyl group, isopropoxycarbonyl group, n-butoxycarbonyl group, tert-butoxycarbonyl group and the like. The trialkylsilyl group is a silyl group substituted by the same or different three or more of the above-described alky groups and examples thereof include a trimethylsilyl group, tert-butyldimethylsilyl group and the like. It is preferable that $R^3$ is a hydrogen atom and $R^4$ is a nitro group, and particularly, it is more preferable that the nitro group represented by $R^4$ is linked to the 5-position on the connected phenyl group.

Examples of the salicylidene amino alcohol compound (1) include optically active salicylidene amino alcohol compounds such as N-(5-nitrosalicylidene)-2-amino-1,1-di(5-tert-butyl-2-n-butoxyphenyl)-1-propanol, N-(3,5-dichlorosalicylidene)-2-amino-1,1-diphenyl-1-propanol, N-(3-fluorosalicylidene)-2-amino-1,1-diphenyl-1-propanol, N-(5-nitrosalicylidene)-2-amino-1,1-di(2-methoxyphenyl)-1-propanol, N-(3,5-dichlorosalicylidene)-2-amino-1,1-di(2-methoxyphenyl)-1-propanol, N-(3-fluorosalicylidene)-2-amino-1,1-di(2-methoxyphenyl)-1-propanol, N-(5-nitrosalicylidene)-2-amino-1,1-di(5-tert-butyl-2-n-butoxyphenyl)-1-propanol, N-(3,5-dichlorosalicylidene)-2-amino-1,1-di(5-tert-butyl-2-n-butoxyphenyl)-1-propanol, N-(3-fluorosalicylidene)-2-amino-1,1-di(5-tert-butyl-2-n-butoxyphenyl)-1-propanol, N-(5-nitrosalicylidene)-2-amino-1,1-di(5-tert-butyl-2-tert-butoxyphenyl)-1-propanol, N-(3,5-dichlorosalicylidene)-2-amino-1,1-di(5-tert-butyl-2-tert-butoxyphenyl)-1-propanol, N-(3-fluorosalicylidene)-2-amino-1,1-di(5-tert-butyl-2-tert-butoxyphenyl)-1-propanol, N-(5-nitrosalicylidene)-2-amino-1,1-di(5-tert-butyl-2-octyloxyphenyl)-1-propanol, N-(3,5-dichlorosalicylidene)-2-amino-1,1-di(5-tert-butyl-2-octyloxyphenyl)-1-propanol, N-(3-fluorosalicylidene)-2-amino-1,1-di(5-tert-butyl-2-octyloxyphenyl)-1-propanol, N-(5-nitrosalicylidene)-2-amino-1,1-dibenzyl-1-propanol, N-(3,5-dichlorosalicylidene)-2-amino-1,1-dibenzyl-1-propanol, N-(3-fluorosalicylidene)-2-amino-1,1-dibenzyl-1-propanol, N-(5-nitrosalicylidene)-2- amino-1,1-di(2-methoxybenzyl)-1-propanol, N-(3,5-dichlorosalicylidene)-2-amino-1,1-di(2-methoxybenzyl)-1-propanol, N-(3-fluorosalicylidene)-2-amino-1,1-di(2-methoxybenzyl)-1-propanol, N-(5-nitrosalicylidene)-2-amino-1,1-di(5-tert-butyl-2-n-octyloxyphenyl)-3-phenyl-1-propanol, N-salicylidene-2-amino-1,1-di(5-tert-butyl-2-n-butoxyphenyl)-1-propanol, N-(5-fluorosalicylidene)-2-amino-1,1-di(5-tert-butyl-2-n-butoxyphenyl)-1-propanol, N-(5-chlorosalicylidene)-2-amino-1,1-di(5-tert-butyl-2-n-butoxyphenyl)-1-propanol, N-(5-methoxycarbonylsalicylidene)-2-amino-1,1-di(5-tert-butyl-2-n-butoxyphenyl)-1-propanol, N-(5-ethoxycarbonylsalicylidene)-2-amino-1,1-di(5-tert-butyl-2-n-butoxyphenyl)-1-propanol, N-[5-(n-propoxycarbonyl)salicylidene]-2-amino-1,1-di(5-tert-butyl-2-n-butoxyphenyl)-1-propanol, N-(5-isopropoxycarbonylsalicylidene)-2-amino-1,1-di(5-tert-butyl-2-n-butoxyphenyl)-1-propanol, N-(5-fluoromethylsalicylidene)-2-amino-1,1-di(5-tert-butyl-2-n-butoxyphenyl)-1-propanol, N-(5-difluoromethylsalicylidene)-2-amino-1,1-di(5-tert-butyl-2-n-butoxyphenyl)-1-propanol, N-(5-trifluoromethylsalicylidene)-2-amino-1,1-di(5-tert-butyl-2-n-butoxyphenyl)-1-propanol, N-salicylidene-2-amino-1,1-di(5-tert-butyl-2-n-butoxyphenyl)-3-phenyl-1-propanol, N-(5-fluorosalicylidene)-2-amino-1,1-di(5-tert-butyl-2-n-butoxyphenyl)-3-phenyl-1-propanol, N-(5-chlorosalicylidene)-2-amino-1,1-di(5-tert-butyl-2-n-butoxyphenyl)-3-phenyl-1-propanol, N-(5-methoxycarbonylsalicylidene)-2-amino-1,1-di(5-tert-butyl-2-n-butoxyphenyl)-3-phenyl-1-propanol, N-(5-ethoxycarbonylsalicylidene)-2-amino-1,1-di(5-tert-butyl-2-n-butoxyphenyl)-3-phenyl-1-propanol, N-[5-(n-propoxycarbonyl)salicylidene]-2-amino-1,1-di(5-tert-butyl-2-n-butoxyphenyl)-3-phenyl-1-propanol, N-(5-isopropoxycarbonylsalicylidene)-2-amino-1,1-di(5-tert-butyl-2-n-butoxyphenyl)-3-phenyl-1-propanol, N-(5-fluoromethylsalicylidene)-2-amino-1,1-di(5-tert-butyl-2-n-butoxyphenyl)-3-phenyl-1-propanol, N-(5-difluoromethylsalicylidene)-2-amino-1,1-di(5-tert-butyl-2-n-butoxyphenyl)-3-phenyl-1-propanol, N-(5-trifluoromethylsalicylidene)-2-amino-1,1-di(5-tert-butyl-2-n-butoxyphenyl)-3-phenyl-1-propanol, N-salicylidene-2-amino-1,1-di(5-tert-butyl-2-n-octyloxyphenyl)-1-propanol, N-(5-fluorosalicylidene)-2-amino-1,1-di(5-tert-butyl-2-n-octyloxyphenyl)-1-propanol, N-(5-chlorosalicylidene)-2-amino-1,1-di(5-tert-butyl-2-n-octyloxyphenyl)-1-propanol, N-(5-methoxycarbonylsalicylidene)-2-amino-1,1-di(5-tert-butyl-2-n-octyloxyphenyl)-1-propanol, N-(5-ethoxycarbonylsalicylidene)-2-amino-1,1-di(5-tert-butyl-2-n-octyloxyphenyl)-1-propanol, N-[5-(n-propoxycarbonyl)salicylidene]-2-amino-1,1-di(5-tert-butyl-2-n-octyloxyphenyl)-1-propanol, N-(5-isopropoxycarbonylsalicylidene)-2-amino-1,1-di(5-tert-butyl-2-n-octyloxyphenyl)-1-propanol, N-(5-fluoromethylsalicylidene)-2-amino-1,1-di(5-tert-butyl-2-n-octyloxyphenyl)-1-propanol, N-(5-difluoromethylsalicylidene)-2-amino-1,1-di(5-tert-butyl-2-N-octyloxyphenyl)-1-propanol, N-(5-trifluoromethylsalicylidene)-2-amino-1,1-di(5-tert-butyl-2-n-octyloxyphenyl)-1-propanol, N-salicylidene-2-amino-1,1-di(5-tert-butyl-2-n-octyloxyphenyl)-3-phenyl-1-propanol, N-(5-fluorosalicylidene)-2-amino-1,1-di(5-tert-butyl-2-n-octyloxyphenyl)-3-phenyl-1-propanol, N-(5-chlorosalicylidene)-2-amino-1,1-di(5-tert-butyl-2-n-octyloxyphenyl)-3-phenyl-1-propanol, N-(5-methoxycarbonylsalicylidene)-2-amino-1,1-di(5-tert-butyl-2-n-octyloxyphenyl)-3-phenyl-1-propanol, N-(5-ethoxycarbonylsalicylidene)-2-amino-1,1-di(5-tert-butyl-2-n-octyloxyphenyl)-3-phenyl-1-propanol, N-[5-(n-propoxycarbonyl)salicylidene]-2-amino-1,1-di(5-tert-butyl-2-n-octyloxyphenyl)-3-phenyl-1-propanol, N-(5-isopropoxycarbonylsalicylidene)-2-amino-1,1-di(5-tert-butyl-2-n-octyloxyphenyl)-3-phenyl-1-propanol, N-(5-fluoromethylsalicylidene)-2-amino-1,1-di(5-tert-butyl-2-n-octyloxyphenyl)-3-phenyl-1-propanol, N-(5-difluoromethylsalicylidene)-2-amino-1,1-di(5-tert-butyl-2-n-octyloxyphenyl)-3-phenyl-1-propanol, N-(5-trifluoromethylsalicylidene)-2-amino-1,1-di(5-tert-butyl-2-n-octyloxyphenyl)-3-phenyl-1-propanol, N-(6-trimethylsilylsalicylidene)-2-amino-1,1-di(5-tert-butyl-2-n-butoxyphenyl)-1-propanol, N-(6-tert-butyldimethylsilylsalicylidene)-2-amino-1,1-di(5-tert-butyl-2-n-butoxyphenyl)-1-propanol, N-(6-trimethylsilylsalicylidene)-2-amino-1,1-di(5-tert-butyl-2-n-butoxyphenyl)-3-phenyl-1-propanol, N-(6-tert-butyldimethylsilylsalicylidene)-2-amino-1,1-di(5-tert-butyl-2-n-butoxyphenyl)-3-phenyl-1-propanol, N-(6-trimethylsilylsalicylidene)-2-amino-1,1-di(5-tert-butyl-2-n-octyloxyphenyl)-1-propanol, N-(6-tert-butyldimethylsilylsalicylidene)-2-amino-1,1-di(5-tert-butyl-2-n-octyloxyphenyl)-1-propanol, N-(6-trimethylsilylsalicylidene)-2-amino-1,1-di(5-tert-butyl-2-n-octyloxyphenyl)-3-phenyl-1-propanol, N-(6-tert-butyldimethylsilylsalicylidene)-2-amino-1,1-di(5-tert-butyl-2-n-octyloxyphenyl)-3-phenyl-1-propanol, N-(3-fluorosalicylidene)-2-amino-1,1-di(5-tert-butyl-2-n-butoxyphenyl)-3-phenyl-1-propanol, N-(3-chlorosalicylidene)-2-amino-1,1-di(5-tert-butyl-2-n-butoxyphenyl)-3-phenyl-1-propanol, N-salicylidene-2-amino-1,1-diphenyl-1-propanol, N-(3-methoxy-5-nitrosalicylidene)-2-amino-1,1-diphenyl-1-propanol, N-(3,5-dinitrosalicylidene)-2-amino-1,1-diphenyl-1-propanol, N-(5-nitrosalicylidene)-2-amino-1,1-di(2-methoxyphenyl)-1-propanol, N-(3,5-dichlorosalicylidene)-2-amino-1,1-di(2-methoxyphenyl)-1-propanol, N-(5-nitrosalicylidene)-2-amino-1,1-di(2-methoxyphenyl)-3-methyl-1-butanol, N-(3,5-di-tert-butylsalicylidene)-2-amino-1,1-di(2-methoxyphenyl)-1-propanol, and the like. The salicylidene amino alcohol compound (1) includes R-form and S-form optically active substances, and in the present invention, any of them may be used, and a mixture of them may also be used. The salicylidene amino alcohol compound (1) can be produced using any known methods.

As the copper compound, usually, a divalent copper compound is used, and examples thereof include copper(II) acetate, copper(II) trifluoroacetate, copper(II) bromide, copper(II) chloride, copper(II) hydroxide and the like. These may be used singly or in admixture of two or more, and copper(II) acetate or copper(II) hydroxide is preferable, and copper(II) acetate is more preferable. As the copper compound, commercially available compounds can be usually used.

The use amount of the copper compound is usually in the range of 0.9 to 1.5 mole ratio, preferably 0.9 to 1.2 mole ratio with respect to the salicylidene amino alcohol compound (1).

The reaction of a salicylidene amino alcohol compound (1) with a copper compound (in the present specification, referred to a complexation reaction in some cases) is usually carried out in the presence of a solvent. Such a solvent is not particularly restricted providing it is a solvent inert to the reaction, and examples thereof include aromatic hydrocarbon solvents such as toluene, xylene and the like; ester solvents such as methyl acetate, ethyl acetate and the like; halogenated hydrocarbon solvents such as dichloromethane, chloroform, dichloroethane and the like; aliphatic hydrocarbon solvents such as hexane, heptane and the like; alcohol solvents such as methanol, ethanol and the like; and the like. These may be used singly or in combination of two or more. Water may also be used together, and in the case of use of copper(II) hydroxide as the copper compound, it is preferable to use water together. The use amount of such a solvent is not particularly restricted, and it is usually in the range of 1 to 100 weight ratio, preferably 2 to 10 weight ratio with respect to the salicylidene amino alcohol compound (1).

This reaction is usually carried out by mixing a salicylidene amino alcohol compound (1) and a copper compound in the presence of a solvent, and the mixing order thereof is not particularly restricted.

The reaction temperature is usually in the range of 15 to 120° C., preferably 20 to 100° C.

The progress of the reaction can be confirmed by using a usual analysis means such as, for example, liquid chromatography and the like.

By such a reaction, a reaction mixture containing an asymmetric copper complex is obtained. After completion of the reaction, the reaction mixture may be subjected as it is to a crystallization treatment, or may be subjected to a crystallization treatment after performing a post treatment. In the case of use of an alcohol solvent as the above-described solvent, it is preferable that the reaction mixture is subjected as it is to a crystallization treatment. In the case of use of a solvent other than alcohol solvents, the reaction mixture usually contains by-products such as an acid and the like, and an unreacted copper compound and the like, thus, it is preferable to carry out a post treatment to remove them. As such a post treatment operation, for example, operations of mixing water or basic aqueous solution with a reaction mixture, then, carrying out a liquid separation treatment, and the like, are mentioned. Such a post treatment may be carried out repeatedly.

As the reaction mixture to be subjected to such a post treatment, a mixture after the reaction is usually used as it is, and if necessary, it may also be subjected to a concentration treatment, or mixed with a water-insoluble organic solvent. Examples of the water-insoluble organic solvent include aromatic hydrocarbon solvents such as toluene, xylene and the like; ester solvents such as methyl acetate, ethyl acetate and the like; halogenated hydrocarbon solvents such as dichloromethane, chloroform, dichloroethane and the like; aliphatic hydrocarbon solvents such as hexane, heptane and the like; etc.

Examples of the base to be used in the above-described basic aqueous solution include alkali metal hydroxides such as sodium hydroxide, potassium hydroxide and the like; alkali metal carbonates such as sodium carbonate, potassium carbonate and the like; alkali metal hydrogen carbonates such as sodium hydrogen carbonate, potassium hydrogen carbonate and the like; and the like, and preferable are alkali metal hydrogen carbonates. The use amount of these bases is usually in the range of 2 to 6 mole ratio, preferably 3 to 5 mole ratio with respect to the copper compound.

It may also be permissible to remove insoluble components by performing a filtration treatment, before and after or during the stage of the above-described mixing and liquid separation treatment. Such a filtration treatment can be carried out also using a filtration aid such as diatomaceous earth, alumina or the like, and the use amount thereof is not particularly restricted.

The crystallization treatment in the present invention is carried out in the presence of an alcohol solvent. A reaction mixture post-treated if necessary may be subjected as it is to the crystallization treatment, or may be subjected to the crystallization treatment after a concentration treatment thereof. In the case of use of an alcohol solvent as the above-described solvent, it is preferable that the reaction mixture is subjected at it is to a crystallization treatment. In the case of use of a solvent other than alcohol solvents, it is preferable that the reaction mixture is subjected to a crystallization treatment after a concentration treatment thereof. It is more preferable that the reaction mixture is concentrated to an extent of substantially no inclusion of the above-described solvent other than alcohol solvents, before performing a crystallization treatment. The reaction mixture post-treated if necessary is subjected, if necessary, to a concentration treatment and mixed with an alcohol solvent, then, further subjected to a concentration treatment, thus, a solvent other than alcohol solvents can also be removed by azeotropy with an alcohol solvent. In the case of performing such an azeotropy operation, an alcohol solvent remaining in the reaction mixture after a concentration treatment can be used as it is in a crystallization treatment.

Examples of the alcohol solvent to be used in a crystallization treatment include alcohols having 1 to 4 carbon atoms such as methanol, ethanol, n-propanol, isopropanol, n-butanol, tert-butanol and the like, and preferable is methanol. In the case of use of an alcohol solvent as the solvent in the above-described reaction, the solvent can be used as it is in a crystallization treatment. The use amount of an alcohol solvent is not particularly restricted, and usually in the range of 1 to 100 weight ratio, preferably 5 to 20 weight ratio with respect to the salicylidene amino alcohol compound (1).

The crystallization treatment operation is usually carried out by mixing an alcohol solvent and a reaction mixture subjected, if necessary, to the above-described post treatment and/or concentration treatment, and the mixing order thereof is not particularly restricted. The temperature in the crystallization treatment is usually in the range of −50 to 80° C., preferably −10 to 60° C. In the case of immediate deposition of a crystal by mixing of a reaction mixture and an alcohol solvent, the mixture may be subjected as it is to a solid-liquid separation treatment described later, or may be further cooled in the above-described temperature range. It is more preferable that a reaction mixture and an alcohol solvent are mixed in the range of 30 to 60° C. to obtain a solution containing an intended asymmetric copper complex, and the solution is cooled down to the range of −10 to 20° C. to cause deposition of a crystal. In this case, an intended asymmetric copper complex crystal may be used as a seed crystal. The seed crystal may be added after mixing of a reaction mixture and an alcohol solvent, or added during the mixing stage.

After completion of the crystallization treatment, an intended asymmetric copper complex crystal can be collected from the resultant mixture by, for example, a usual solid-liquid separation treatment such as filtration treatment and the like. The resultant asymmetric copper complex crystal may be further subjected to a washing treatment. The solvent to be used in the washing treatment is not particularly restricted, and usually, alcohols solvents exemplified as the solvent to be used in the above-described crystallization treatment are used.

The collected asymmetric copper complex crystal shows catalytic activity, for example, in a reaction of prochiral olefins and diazoacetates.

Next, preferable production method examples of the salicylidene amino alcohol compound (1) to be used in the present invention will be illustrated.

A salicylidene amino alcohol compound (1) can be obtained by reacting an optically active amino alcohol compound of the formula (2):

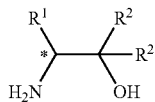
(2)

(wherein, $R^1$, $R^2$ and * represent the same meanings as described above.)
(hereinafter, abbreviated as amino alcohol compound (2)) with a salicylaldehyde compound of the formula (3):

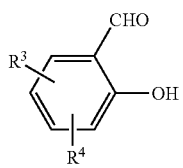
(3)

(wherein, $R^3$ and $R^4$ represent the same meanings as described above.)
(hereinafter, abbreviated as salicylaldehyde compound (3)).

Examples of the amino alcohol compound (2) include optically active amino alcohol compounds such as 2-amino-1,1-diphenyl-1-propanol, 2-amino-1,1-di(2-methoxyphenyl)-1-propanol, 2-amino-1,1-di(5-tert-butyl-2-n-butoxyphenyl)-1-propanol, 2-amino-1,1-di(5-tert-butyl-2-tert-butoxyphenyl)-3-phenyl-1-propanol, 2-amino-1,1-di(5-tert-butyl-2-octyloxyphenyl)-1-propanol, 2-amino-1,1-dibenzyl-1-propanol, 2-amino-1,1-di(methoxybenzyl)-1-propanol, and the like. The amino alcohol compound (2) includes R-form and S-form optically active substances, and may be appropriately selected depending on the intended salicylidene amino alcohol compound (1). The amino alcohol compound (2) can be produced using any known methods.

Examples of the salicylaldehyde compound (3) include 2-hydroxy-benzaldehyde, 2-hydroxy-5-nitrobenzaldehyde, 2-hydroxy-3,5-dichlorobenzaldehyde, 2-hydroxy-3-fluorobenzaldehyde, 2-hydroxy-3-chlorobenzaldehyde, 2-hydroxy-3-methoxy-5-nitrobenzaldehyde, 2-hydroxy-3,5-di-tert-butylbenzaldehyde, 2-hydroxy-5-fluorobenzaldehyde, 2-hydroxy-5-chlorobenzaldehyde, 2-hydroxy-5-methoxycarbonylbenzaldehyde, 2-hydroxy-5-ethoxycarbonylbenzaldehyde, 2-hydroxy-5-(n-propoxycarbonyl)benzaldehyde, 2-hydroxy-isopropoxycarbonylbenzaldehyde, 2-hydroxy-5-fluoromethylbenzaldehyde, 2-hydroxy-5-difluoromethylbenzaldehyde, 2-hydroxy-5-trifluoromethylbenzaldehyde, 2-hydroxy-6-trimethylsilylbenzaldehyde, 2-hydroxy-6-tert-butyldimethylsilylbenzaldehyde, and the like. As the salicylaldehyde compound (3), commercially available compounds can be used, and it can be produced using any known methods.

The use amount of the salicylaldehyde compound (3) is usually in the range of 0.9 to 2 mole ratio, preferably 1.0 to 1.2 mole ratio with respect to the amino alcohol compound (2).

The reaction of the amino alcohol compound (2) and the salicylaldehyde compound (3) is usually carried out in the presence of a solvent. Examples of such a solvent include aromatic hydrocarbon solvents such as toluene, xylene, benzene and the like; halogenated hydrocarbon solvents such as chlorobenzene, chloroform, dichloromethane and the like; alcohol solvents such as methanol, ethanol and the like; ether solvents such as methyl-tert-butyl ether, diethyl ether, tetrahydrofuran and the like; etc. These solvents may be used singly or in admixture. The use amount thereof is not particularly restricted.

The reaction of the amino alcohol compound (2) and the salicylaldehyde compound (3) is carried out by mixing both the compounds, if necessary, in the presence of a solvent, and usually, the mixing order thereof is not particularly restricted.

The reaction temperature is usually in the range of 15 to 150° C., preferably 20 to 120° C.

The progress of the reaction can be confirmed using usual analysis means such as, for example, gas chromatography, liquid chromatography and the like.

The reaction mixture after completion of the reaction contains a salicylidene amino alcohol compound (1), and it may be used as it is, or the salicylidene amino alcohol compound (1) may be isolated by a concentration treatment and the like. The isolated salicylidene amino alcohol compound (1) may be further purified using means such as crystallization treatment, column chromatography and the like before use.

Next, preferable production method examples of the above-described amino alcohol compound (2) will be illustrated.

An amino alcohol compound (2) can be obtained by reacting an optically active amino acid ester compound of the formula (4):

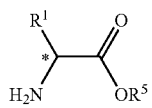
(4)

(wherein, $R^1$ and * represent the same meanings as described above, and $R^5$ represents an optionally substituted alkyl group or optionally substituted phenyl group.)
(hereinafter, abbreviated as amino acid ester compound (4)) with a Grignard compound of the formula (5):

$R^2$—MgX (5)

(wherein, $R^2$ represents the same meaning as described above, and X represents a halogen atom.)
(hereinafter, abbreviated as Grignard compound (5)).

Examples of the alkyl group represented by $R^5$ in the formula (4) include alkyl groups having 1 to 4 carbon atoms such as a methyl group, ethyl group, n-propyl group, isopropyl group, n-butyl group, tert-butyl group and the like. Such an alkyl group is optionally substituted by, for example, an alkoxy group such as a methoxy group, ethoxy group, propoxy group, isopropoxy group and the like, or a phenyl group and the like, and specific examples of the alkyl group substituted by such a substituent include a methoxymethyl group, ethoxymethyl group, methoxyethyl group, benzyl group, trityl group and the like.

Examples of the substituent optionally substituted on a phenyl group represented by $R^5$ include alkyl groups having 1 to 4 carbon atoms such as a methyl group, ethyl group, n-propyl group, isopropyl group, n-butyl group, isobutyl group, sec-butyl group, tert-butyl group and the like; alkoxy groups having 1 to 10 carbon atoms such as a methoxy group, ethoxy group, n-propoxy group, isopropoxy group, n-butoxy group, isobutoxy group, sec-butoxy group, tert-butoxy group, n-pentyloxy group, n-hexyloxy group, n-octyloxy group, isooctyloxy group, n-decyloxy group and the like; etc. Specific examples of the phenyl group substituted by such a substituent include a 2-methoxyphenyl group, 2-n-butoxy-5-tert-butylphenyl group, 2-tert-butoxy-5-tert-butylphenyl group, 2-n-octyloxy-5-tert-butylphenyl group and the like.

Examples of the halogen atom represented by X in the formula (5) include a fluorine atom, chlorine atom, bromine atom and the like, and preferable is a bromine atom.

Examples of the amino acid ester compound (4) include an alanine benzyl ester, phenylalanine benzyl ester, valine benzyl ester, isoleucine benzyl ester and leucine benzyl ester, and optically active compounds obtained by substituting a benzyl ester part of the above-described compounds by a methyl ester, ethyl ester, n-propyl ester, isopropyl ester, n-butyl ester, tert-butyl ester, phenyl ester, 2-methoxyphenyl ester, 2-n-butoxy-5-tert-butylphenyl ester, 2-tert-butoxy-5-tert-butylphenyl ester, 2-n-octyloxy-5-tert-butylphenyl ester, 2-methylbenzyl ester, 3-methylbenzyl ester, 4-methylbenzyl ester, 4-ethylbenzyl ester, 4-propylbenzyl ester, 4-isopropylbenzyl ester, 4-n-butylbenzyl ester, 4-tert-butylbenzyl ester, 4-pentylbenzyl ester, 4-hexylbenzyl ester, 2,3-dimethylbenzyl ester, 2,4-dimethylbenzyl ester, 2,5-dimethylbenzyl ester, 3,4-dimethylbenzyl ester, 3,5-dimethylbenzyl ester, 2-methoxybenzyl ester, 3-methoxybenzyl ester, 4-methoxybenzyl ester, 4-ethoxybenzyl ester, 4-propoxybenzyl ester, 4-isopropoxybenzyl ester, 4-n-butoxybenzyl ester, 4-tert-butoxybenzyl ester, 4-pentyloxybenzyl ester, 4-hexyloxybenzyl ester, 2,3-dimethoxybenzyl ester, 2,4-dimethoxybenzyl ester, 2,5-dimethoxybenzyl ester, 3,4-dimethoxybenzyl ester, 3,5-dimethoxybenzyl ester, 4-nitrobenzyl ester, 4-cyanobenzyl ester, 4-fluorooxybenzyl ester and 4-chlorooxybenzyl ester, and the like. The amino acid ester compound (4) includes R-form and S-form optically active substances, and may be appropriately selected depending on the intended amino alcohol compound (2).

As the amino acid ester compound (4), commercially available compounds may be used, and for example, compounds obtained by reacting an optically active amino acid of the formula (6):

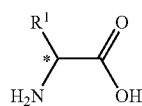

(6)

(wherein, R$^5$ and * represent the same meanings as described above.)

with a hydroxyl compound of the formula (7):

(7)

(wherein, R$^5$ represents the same meaning as described above.)

in the presence of an acid may be used. As the acid, organic sulfonic acids such as methanesulfonic acid, p-toluenesulfonic acid and the like are usually used, and preferable is p-toluenesulfonic acid. The amino acid ester compound (4) obtained by this method is usually an addition salt with an acid used in the reaction, and this can be subjected as it is to a reaction with a Grignard compound (5), however, it is necessary to use the Grignard compound (5) in excess amount, thus, the addition salt of the amino acid ester compound (4) and the acid is preferably treated with a base before use. (hereinafter, treatment of the addition salt of the amino acid ester compound (4) and the acid with a base is abbreviated simply as "base treatment" in some cases.).

Examples of the base include tertiary amine compounds such as triethylamine, pyridine and the like; alkali metal hydroxides such as sodium hydroxide, potassium hydroxide and the like; alkali metal carbonates such as sodium carbonate, potassium carbonate and the like; alkali metal hydrogen carbonates such as sodium hydrogen carbonate, potassium hydrogen carbonate and the like; etc. The alkali metal hydroxides, alkali metal carbonates or alkali metal hydrogen carbonates are usually used in the form of aqueous solution, and the concentration thereof is not particularly restricted. Preferable are tertiary amine compounds, and more preferable is triethylamine. The use amount of the base is usually in the range of 1 to 2 mole ratio, preferably 1.1 to 1.3 mole ratio with respect to the addition salt of the amino acid ester compound (4) and the acid.

The above-described base treatment is carried out usually in the presence of an organic solvent. Examples of the organic solvent include aliphatic hydrocarbon solvents such as hexane, heptane, cyclohexane and the like; aromatic solvents such as toluene, xylene, monochlorobenzene, dichlorobenzene, trifluorotoluene and the like; ether solvents such as methyl tert-butyl ether, diethyl ether and the like; halogenated hydrocarbon solvents such as dichloromethane, dichloroethane, chlorobutane and the like; ester solvents such as ethyl acetate, butyl acetate and the like; etc. The base treatment may also be carried out in a two-layer system composed of an organic solvent and water. The use amounts of the organic solvent and water are usually in the range of 1 to 100 weight ratio, preferably 5 to 10 weight ratio with respect to the addition salt of the amino acid ester compound (4) and the acid.

The base treatment temperature is usually in the range of −10 to 40° C., preferably 0 to 10° C.

The mixture after the base treatment is subjected as it is to a liquid separation treatment, or the mixture after the base treatment is mixed if necessary with a water-insoluble organic solvent or water before being subjected to a liquid separation treatment. By this procedure, a solution of an amino acid ester compound (4) is obtained as an organic layer. Here, a solution of an amino acid ester compound (4) may further be obtained as an organic layer, by performing an extraction treatment of an aqueous layer after the liquid separation treatment, using a water-insoluble organic solvent. This extraction treatment may be carried out repeatedly. The temperature of the treating substance in the liquid separation treatment or the extraction treatment is usually in the range of −10 to 40° C., preferably 0 to 10° C.

As the water-insoluble organic solvent, the same solvents as the organic solvents used in the above-described base treatment are mentioned, and the use amount thereof is not particularly restricted.

Thus obtained solution of an amino acid ester compound (4) is, if necessary, subjected to a concentration treatment. The condition of the concentration treatment includes usually in the range of 20 to 45° C., preferably 30 to 40° C. under reduced pressure. The concentration of an amino acid ester compound (4) in the solution after the concentration treatment is usually in the range of 1 to 45 wt %, preferably 5 to 30 wt %.

In general, the amino acid ester compound (4) is a compound which is unstable under condition of formation of no addition salt with an acid, and usually generates easily by-products such as a dimer of the formula (8):

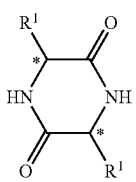

(8)

(wherein, $R^1$ and * represent the same meanings as described above.)

and the like. In the case of carrying out the base treatment under the above-described condition, and if necessary the concentration treatment, however, an amino acid ester compound (4) can be taken out efficiently in the form of solution containing a free body which is not an addition salt with an acid, and this can be used as it is in the reaction with a Grignard compound (5).

Examples of the Grignard compound (5) include phenylmagnesium chloride, phenylmagnesium bromide, 5-tert-butyl-2-n-butoxyphenylmagnesium chloride, 5-tert-butyl-2-n-butoxyphenylmagnesium bromide, 2-methoxyphenylmagnesium chloride, 2-methoxyphenylmagnesium bromide, 5-tert-butyl-2-tert-butoxyphenylmagnesium chloride, 5-tert-butyl-2-tert-butoxyphenylmagnesium bromide, 5-tert-butyl-2-octyloxyphenylmagnesium chloride, 5-tert-butyl-2-octyloxyphenylmagnesium bromide, benzylmagnesium chloride, benzylmagnesium bromide, 2-methoxybenzylmagnesium chloride, 2-methoxybenzylmagnesium bromide and the like.

As the Grignard compound (5), commercially available compounds may be used, and for example, compounds obtained by reacting an organic halogen compound of the formula (9):

$$R^2—X \quad (9)$$

(wherein, $R^2$ and X represent the same meanings as described above.)

with a metal magnesium may be used.

The use amount of the Grignard compound (5) is usually in the range of 2 to 10 mole ratio, preferably 3 to 5 mole ratio with respect to the amino acid ester compound (4).

The reaction of the amino acid ester compound (4) and the Grignard compound (5) is usually carried out in the presence of a solvent. As the solvent, those inert to the reaction are advantageous, and examples thereof include ether solvents such as methyl tert-butyl ether, diethyl ether, tetrahydrofuran and the like; aromatic hydrocarbon solvents such as toluene, xylene, benzene and the like; aliphatic hydrocarbon solvents such as hexane, heptane and the like; etc., used singly or in admixture, and the use amount thereof is not particularly restricted.

The reaction of the amino acid ester compound (4) and the Grignard compound (5) are carried out by mixing both the compounds, if necessary in the presence of a solvent, and usually, the mixing order thereof is not particularly restricted, however, it is preferable that the amino acid ester compound (4) is added to the Grignard compound (5). An embodiment of adding the amino acid ester compound (4) to the Grignard compound (5) continuously or intermittently is more preferable.

The reaction temperature is usually in the range of 0 to 100° C., preferably 10 to 30° C.

The progress of the reaction can be confirmed using usual analysis means such as, for example, gas chromatography, liquid chromatography and the like.

The reaction mixture includes inorganic substances such as a magnesium salt and the like which are by-produced by the progress of the reaction, and if necessary, the reaction mixture after completion of the reaction is post-treated for the purpose of removing the inorganic substances. The post treatment is usually carried out using an acid and, if necessary a base, and it is preferable that the reaction mixture is treated with an acid, then, treated with a base.

Examples of the acid to be used in such a post treatment include inorganic acids such as hydrochloric acid, hydrobromic acid, sulfuric acid, phosphoric acid and the like, and organic acids such as acetic acid, citric acid and the like. These acids are usually used in the form of aqueous solution, and the concentration thereof is not particularly restricted. An aqueous solution of an inorganic acid is preferable. The use amount of the acid is usually in the range of 1 to 100 mole ratio, preferably 2 to 10 mole ratio with respect to an amino acid ester compound (4).

Examples of the base include alkali metal hydroxides such as sodium hydroxide, potassium hydroxide and the like; alkali metal carbonates such as sodium carbonate, potassium carbonate and the like; alkali metal hydrogen carbonates such as sodium hydrogen carbonate, potassium hydrogen carbonate and the like; ammonia; and the like. The alkali metal hydroxides, alkali metal carbonates or alkali metal hydrogen carbonates are used usually in the form of aqueous solution, and the concentration thereof is not particularly restricted. Regarding the ammonia, one in gaseous form may be used, or ammonia water may be used.

Further, it may be dissolved in an alcohol such as methanol and the like. Ammonia water is preferable. The concentration of ammonia water is usually 5 to 50 wt %, preferably 10 to 30 wt %. The use amount of the base varies depending on the use amount of the above-described acid, and may advantageously be a value at which pH of an aqueous layer of treating liquid is in the range of usually 8 or more, preferably 8.5 to 9.0.

As a specific operation of the post treatment, for example, a reaction mixture and an aqueous solution of an acid are mixed and the mixture is subjected to a liquid separation treatment, then, the resultant organic layer and an aqueous solution of a base are mixed and the mixture is subjected to a liquid separation treatment. This post treatment operation may be carried out repeatedly, and, in the intermediate stage or final stage, a washing treatment may be carried out using water, saline and the like. The temperature of the treated substance during the above-described post treatment operation is usually in the range of 0 to 40° C., preferably 10 to 30° C.

The reaction mixture post-treated if necessary contains an amino alcohol compound (2) and this may be used as it is, or the amino alcohol compound (2) may be isolated by a concentration treatment and the like. When the reaction mixture post-treated if necessary contains impurities, it may be advantageous that, for example, impurities are removed by a solid-liquid separation treatment such as a filtration treatment and the like, then, the reaction mixture is used as it is, or subjected to a concentration treatment or the like. In the case of performing a concentration treatment, for example, filtration aids such as diatomaceous earth, alumina and the like can be used, and the use amount thereof is not particularly restricted. The isolated amino alcohol compound (2) may be further purified using means such as a crystallization treatment, column chromatography and the like.

The present invention is industrially advantageous since the present invention is capable of getting an asymmetric copper catalyst crystal with good purity which is useful as a catalyst for asymmetric synthesis using a diazo compound, and the like.

EXAMPLES

The present invention will be illustrated further in detail by examples below, but it is needless to say that the present invention is not limited to these examples.

Example 1

Production of L-Alanine Benzyl Ester

Into a 500 mL separable flask equipped with a thermometer and a stirring apparatus was charged 33.0 g of p-toluenesulfonic acid salt of L-alanine benzyl ester (content analysis value according to high performance liquid chromatography internal standard method: L-alanine benzyl ester 47.7 wt % (87.9 mmol), p-toluenesulfonic acid 50.8 wt %) and 99.0 g of water, these were mixed, then, a nitrogen atmosphere is made in the flask. To the mixture was added 94.5 g of toluene, then, the mixture was cooled to 5° C., and 10.8 g (107 mmol) of triethylamine was dropped over a period of 2 hours while keeping the same temperature. The resultant mixture was stirred at 5° C. for 30 minutes, and allowed to stand still, then, subjected to a liquid separation treatment (organic layer obtained in this stage is referred to as organic layer A). 94.5 g of toluene was charged while keeping the resultant aqueous layer at 5° C., the mixture was stirred at the same temperature for 30 minutes and allowed to stand still, then, subjected to a liquid separation treatment (organic layer obtained in this stage is referred to as organic layer B). The organic layer B was subjected to a concentration treatment under a reduced pressure of 8.0 to 4.7 kPa at an inner temperature of 31 to 42° C., then, the concentrate of the resultant organic layer B, and the organic layer A were mixed, and the mixture was subjected to a concentration treatment under a reduced pressure of 9.3 to 4.0 kPa at an inner temperature of 35 to 42° C., to obtain 60.0 g of a toluene solution containing L-alanine benzyl ester. The solution was analyzed by a high performance liquid chromatography internal standard method to find inclusion of 14.5 g (80.7 mmol) of L-alanine benzyl ester. The yield of L-alanine benzyl ester against p-toluenesulfonic acid salt was 92%.

Example 2

Production of (2S)-2-amino-1,1-di(5-tert-butyl-2-n-butoxyphenyl)-1-propanol An atmosphere in a 100 mL separable flask equipped with a thermometer and a stirring apparatus was purged with nitrogen, and into this, 0.62 g (26 mmol) of magnesium (turnings), 8.06 g of tetrahydrofuran and 16.3 g of toluene were charged and mixed. The mixture was heated up to 75° C., then, a mixture of 0.02 g (0.08 mmol) of iodine and 0.13 g of toluene, and 0.75 g of (2.6 mmol) of 4-tert-butyl-2-bromophenyl-n-butyl ether and 1.00 g of toluene were charged, and the mixture was stirred for 10 minutes at an inner temperature in the range of 72 to 73° C. The mixture was heated up to 80° C., then, into this, 6.74 g (23.6 mmol) of 4-tert-butyl-2-bromophenyl-n-butyl ether was dropped over a period of 25 minutes, and the mixture was further stirred for 75 minutes at 80° C., to obtain 33.5 g of a Grignard mixture.

An atmosphere in a 500 mL separable flask equipped with a thermometer and a stirring apparatus was purged with nitrogen, and into this, 5.74 g (236 mmol) of magnesium (turnings), 29.6 g of tetrahydrofuran and 59.1 g of toluene were charged and mixed. Into the mixture was added 33.5 g of the above-described Grignard mixture, 2.7 g of tetrahydrofuran and 5.38 g of toluene in sequence. The resultant mixture was heated up to 70° C., then, 2.02 g (7.08 mmol) of 4-tert-butyl-2-bromophenyl-n-butyl ether was added and the mixture was stirred for 10 minutes, as a result, the inner temperature rose from 70.2° C. to 74.6° C. The reaction solution was heated up to 80° C., then, 65.4 g (229 mmol) of 4-tert-butyl-2-bromophenyl-n-butyl ether was dropped over a period of 320 minutes, and the mixture was further stirred for 1 hour at 80° C. The resultant mixture was cooled down to 25° C., and 55.7 g of a toluene solution containing 13.4 g (75.0 mmol) of the L-alanine benzyl ester obtained in Example 1 was dropped over a period of 4 hours, then, the mixture was further stirred for 1 hour at the same temperature, to obtain a reaction mixture.

Into a 500 mL separable flask equipped with a thermometer and a stirring apparatus other than the above-described flask was charged 31.3 g (300 mmol) of 35 wt % hydrochloric acid aqueous solution and 97.2 g of water and mixed. The above-described reaction mixture was dropped into the flask over a period of 45 minutes while keeping the inner temperature at 20 to 30° C. After completion of dropping, 8.06 g of toluene was charged, and the mixture was stirred at 25° C. for 10 minutes and allowed to stand still, then, subjected to a liquid separation treatment. To the resultant organic layer was added 121.5 g of 20 wt % saline solution, and the mixture was stirred at 25° C. for 5 minutes and allowed to stand still, then, subjected to a liquid separation treatment. To the resultant organic layer was added 121.5 g of 20 wt % saline solution, then, 4.20 g (69.0 mmol) of 28 wt % ammonia aqueous solution was added to adjust pH of the aqueous layer to 8.78, and the mixture was stirred at 25° C. for 5 minutes and allowed to stand still, then, subjected to a liquid separation treatment. To the resultant organic layer was added 121.5 g of 20 wt % saline solution, and the mixture was stirred at 25° C. for 5 minutes and allowed to stand still, then, subjected to a liquid separation treatment. The resultant organic layer was filtrated using Hyflo Super Cell (registered trade mark), and the filtration residue was washed twice using 8.20 g of toluene. The filtrate and the toluene wash liquid were combined, to obtain 222 g of a solution containing (2S)-2-amino-1,1-di (5-tert-butyl-2-n-butoxyphenyl)-1-propanol. The solution was analyzed by a high performance liquid chromatography internal standard method to find inclusion of 29.2 g (60.3 mmol) of (2S)-2-amino-1,1-di(5-tert-butyl-2-n-butoxyphenyl)-1-propanol. The yield against L-alanine benzyl ester was 80%.

Example 3

Production of (2S)—N-(5-nitrosalicylidene)-2-amino-1,1-di(5-tert-butyl-2-n-butoxyphenyl)-1-propanol Into a 500 mL separable flask equipped with a thermometer and a stirring apparatus was charged 9.79 g (54.8 mmol) of 2-hydroxy-5-nitrobenzaldehyde and, 202 g of a solution containing 26.5 g (58.6 mmol) of (2S)-2-amino-1,1-di(5-tert-butyl-2-n-butoxyphenyl)-1-propanol obtained in Example 2, and mixed. The mixture was stirred at 30° C. for 150 minutes. The resultant reaction mixture was subjected to a concentration treatment under a reduced pressure of 12.0 to 1.9 kPa at an internal temperature of 25 to 45° C., then, the treated substance and toluene were mixed to obtain 105.6 g of a solution containing (2S)—N-(5-nitrosalicylidene)-2-amino-1,1-di(5-tert-butyl-2-n-butoxyphenyl)-1-propanol. The solution was analyzed by a high performance liquid chromatography internal standard method to find inclusion of 32.9 g (52.0 mmol) of (2S)—N-(5-nitrosalicylidene)-2-amino-1,1-di(5-tert-butyl-2-n-butoxyphenyl)-1-propanol. The yield against (2S)-2-amino-1,1-di(5-tert-butyl-2-n-butoxyphenyl)-1-propanol was 95%.

Example 4

Production of [(2S)—N-(5-nitrosalicylidene)-2-amino-1,1-di(5-tert-butyl-2-n-butoxyphenyl)-1-propanol] Copper Complex: Copper(II) Acetate was Used, Water was not Added in Complexation Reaction Into a 200 mL separable flask equipped with a thermometer and a stirring apparatus (hereinafter, described as flask A in some cases) was charged 45.0 g of a toluene solution containing 19.0 g (30.0 mmol) of (2S)—N-(5-nitrosalicylidene)-2-amino-1,1-di(5-tert-butyl-2-n-butoxyphenyl)-1-propanol, and 30.9 g of toluene and 6.59 g (33.0 mmol) of copper(II) acetate monohydrate, and mixed. The mixture was heated up to 80° C. and stirred at the same temperature for 5 hours. The resultant reaction mixture was analyzed by a high performance liquid chromatography absolute calibration curve method to find inclusion of 20.8 g (30 mmol) of [(2S)—N-(5-nitrosalicylidene)-2-amino-1,1-di(5-tert-butyl-2-n-butoxyphenyl)-1-propanol] copper complex. The yield against (2S)—N-(5-nitrosalicylidene)-2-amino-1,1-di(5-tert-butyl-2-n-butoxyphenyl)-1-propanol was 100%. The reaction mixture was cooled down to 25° C., and 109 g of 5 wt % sodium hydrogen carbonate aqueous solution was dropped over a period of 1 hour, then, 3.80 g of Hyflo Super Cell (registered trade mark) was charged, and the mixture was stirred at 25° C. for 1 hour. This slurry solution was further filtrated using Hyflo Super Cell (registered trade mark), and the filtration residue was washed once with 19.0 g of toluene, then, the filtrate was allowed to stand still at 25° C., to cause liquid separation. The resultant organic layer and 139 g of 2 wt % sodium hydrogen carbonate aqueous solution were mixed and stirred at 25° C. for 5 minutes and allowed to stand still, then, subjected to a liquid separation treatment. The resultant organic layer and 139 g of 2 wt % sodium hydrogen carbonate aqueous solution were mixed and stirred at 25° C. for 5 minutes and allowed to stand still, then, subjected to a liquid separation treatment. The resultant organic layer and 102 g of water were mixed and stirred at 25° C. for 5 minutes and allowed to stand still, then, subjected to a liquid separation treatment. The resultant organic layer was concentrated under reduced pressure to obtain 60.8 g of a reaction mixture containing [(2S)—N-(5-nitrosalicylidene)-2-amino-1,1-di(5-tert-butyl-2-n-butoxyphenyl)-1-propanol] copper complex. 2 g of the mixture was sampled, and analyzed by a high performance liquid chromatography internal standard method to find that the content of [(2S)—N-(5-nitrosalicylidene)-2-amino-1,1-di(5-tert-butyl-2-n-butoxyphenyl)-1-propanol] copper complex was 36.2 wt %. To the residual mixture sampled was added methanol, to adjust the content of [(2S)—N-(5-nitrosalicylidene)-2-amino-1,1-di(5-tert-butyl-2-n-butoxyphenyl)-1-propanol] copper complex to 25 wt %.

Into a 200 mL separable flask equipped with a thermometer and a stirring apparatus (hereinafter, described as flask A in some cases) was charged 85.4 g of methanol, and the reaction mixture after the above-described content adjustment was dropped over a period of 1 hour into the flask B while keeping the inner temperature at 10 to 35° C. The flask A which had contained the reaction mixture was washed with 1.90 g of toluene and 9.49 g of methanol, and the washing liquid was added into the flask B and mixed, and the mixture was stirred at 25° C. for 5 minutes. The resultant mixture in the flask B was subjected to reduced pressure to distill of the solvent. The resultant residue and 94.9 g of methanol were mixed under normal pressure, and the mixture was further subjected to a concentration treatment under reduced pressure. This operation was repeated three times. The resultant treated substance and 95.0 g of methanol were mixed, and the resultant mixture was analyzed by a gas chromatography internal standard method to confirm that 79.0 wt % of methanol was contained. Into this, 69.08 g of methanol was dropped at 40° C. over a period of 1 hour, then, the mixture was cooled down to 15° C. over a period of 5 hours, and the mixture was stirred at 15° C. for 2 hours, to cause deposition of a crystal. The resultant crystal was filtrated, then, washed with 28.48 g of methanol three times. The crystal was dried to obtain 17.40 g of [(2S)—N-(5-nitrosalicylidene)-2-amino-1,1-di(5-tert-butyl-2-n-butoxyphenyl)-1-propanol] copper complex. The yield against (2S)—N-(5-nitrosalicylidene)-2-amino-1,1-di(5-tert-butyl-2-n-butoxyphenyl)-1-propanol was 84.1%.

Example 5

Production of [(2S)—N-(5-nitrosalicylidene)-2-amino-1,1-di(5-tert-butyl-2-n-butoxyphenyl)-1-propanol] Copper Complex: Copper(II) Hydroxide was Used, Water was Added in Complexation Reaction Into a 200 mL separable flask equipped with a thermometer and a stirring apparatus was charged 44.3 g of a toluene solution containing 14.0 g (22.1 mmol) of (2S)—N-(5-nitrosalicylidene)-2-amino-1,1-di(5-tert-butyl-2-n-butoxyphenyl)-1-propanol, and 11.8 g of methanol and 2.38 g (24.3 mmol) of copper(II) hydroxide, and mixed. The mixture was heated up to 60° C. and stirred at the same temperature for 5 hours. Into the mixture was charged 1.78 g of water and mixed, and stirred at the same temperature for 5 hours, further, 1.78 g of water was charged and mixed, and stirred for 2 hours. The resultant reaction mixture was analyzed by a high performance liquid chromatography internal standard method to find that the conversion of (2S)—N-(5-nitrosalicylidene)-2-amino-1,1-di(5-tert-butyl-2-n-butoxyphenyl)-1-propanol was 98.0%. The reaction mixture was cooled down to 40° C., and 97.4 g of methanol was added, and the mixture was cooled down to 15° C. over a period of 5 hours, and the mixture was stirred at 15° C. for 2 hours, to cause deposition of a crystal. The resultant crystal was filtrated, then, washed with 21.0 g of methanol three times. The crystal was dried to obtain 11.3 g of [(2S)—N-(5-nitrosalicylidene)-2-amino-1,1-di(5-tert-butyl-2-n-butoxyphenyl)-1-propanol] copper complex. The yield against (2S)—N-(5-nitrosalicylidene)-2-amino-1,1-di(5-tert-butyl-2-n-butoxyphenyl)-1-propanol was 70.0%.

Example 6

Production of [(2S)—N-(5-nitrosalicylidene)-2-amino-1,1-di(5-tert-butyl-2-n-butoxyphenyl)-1-propanol] Copper Complex: Copper(II) Hydroxide was Used, Water was not Added in Complexation Reaction Into a 200 mL separable flask equipped with a thermometer and a stirring apparatus (hereinafter, described as flask A in some cases) was charged 35.8 g of a toluene solution containing 14.0 g (22.1 mmol) of (2S)—N-(5-nitrosalicylidene)-2-amino-1,1-di(5-tert-butyl-2-n-butoxyphenyl)-1-propanol, and 20.2 g of toluene and 2.38 g (24.3 mmol) of copper(II) hydroxide, and mixed. The mixture was heated up to 80° C. and stirred at the same temperature for 8 hours. The resultant reaction mixture was analyzed by a high performance liquid chromatography absolution calibration curve method to find that 9.25 g (13.3 mmol) of [(2S)—N-(5-nitrosalicylidene)-2-amino-1,1-di(5-tert-butyl-2-n-butoxyphenyl)-1-propanol] copper complex was contained. The yield against (2S)—N-(5-nitrosalicylidene)-2-amino-1,1-di(5-tert-butyl-2-n-butoxyphenyl)-1-propanol was 60.2%. Into the mixture was charged 1.19 g of water and mixed, and the mixture was stirred at the same temperature for 5 hours. The solution was analyzed by high performance liquid chromatography to find that 14.2 g (20.5 mmol) of [(2S)—N-(5-nitrosalicylidene)-2-amino-1,1-di(5-tert-butyl-2-n-butoxyphenyl)-1-propanol] copper complex was contained. The yield against (2S)—N-(5-nitrosalicylidene)-2-amino-1,1-di(5-tert-butyl-2-n-butoxyphenyl)-1-propanol was 92.2%. The reaction mixture cooled down to 25° C.

Into a 200 mL separable flask equipped with a thermometer and a stirring apparatus other than the above-described flask (hereinafter, described as flask B in some cases) was charged 63.0 g of methanol, and the reaction mixture after the above-described content adjustment was dropped over a period of 1 hour into the flask B while keeping the inner temperature at 10 to 35° C. The flask which had contained the reaction mixture was washed with 1.40 g of toluene and 7.00 g of methanol, and the washing liquid was added into the flask B and mixed, and the mixture was stirred at 25° C. for 5 minutes. The resultant mixture in the flask B was subjected to reduced pressure to distill off the solvent. The resultant residue and 70.0 g of methanol were mixed under normal pressure, and the mixture was further subjected to a concentration treatment under reduced pressure. Into this was dropped 99.4 g of methanol at 40° C. over a period of 15 minutes, and the mixture was cooled down to 15° C. over a period of 1 hour, and stirred at 15° C. for 30 minutes, to cause deposition of a crystal. The resultant crystal was filtrated, then, washed with 21.0 g of methanol twice. The crystal was dried to obtain 9.25 g of [(2S)—N-(5-nitrosalicylidene)-2-amino-1,1-di(5-tert-butyl-2-n-butoxyphenyl)-1-propanol] copper complex. The yield against (2S)—N-(5-nitrosalicylidene)-2-amino-1,1-di (5-tert-butyl-2-n-butoxyphenyl)-1-propanol was 62.0%.

The invention claimed is:

1. A method of producing an asymmetric copper complex crystal comprising reacting an optically active salicylidene amino alcohol compound of the formula (1):

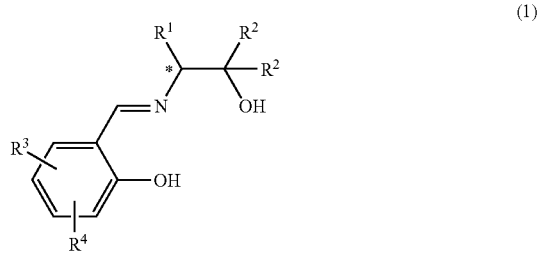

(1)

wherein, $R^1$ represents an alkyl group, aryl group or aralkyl group, $R^2$ represents an optionally substituted alkyl group or optionally substituted phenyl group, $R^3$ and $R^4$ are the same or mutually different and represent a hydrogen atom, halogen atom, nitro group, alkyl group, fluoroalkyl group, alkoxy group, alkoxycarbonyl group, trialkylsilyl group or cyano group, and * represents that the carbon atom is an optically active point with a copper compound, then, performing a crystallization treatment in the presence of an alcohol solvent, wherein the optically active salicylidene amino alcohol compound of the formula (1) is a compound obtained by reacting an optically active amino alcohol compound of the formula (2):

(2)

with a salicylaldehyde compound of the formula (3):

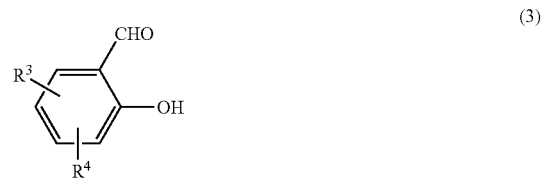

(3)

wherein the optically active amino alcohol compound of the formula (2) is a compound obtained by reacting an optically active amino acid ester compound of the formula (4):

(4)

wherein, $R^1$ and * represent the same meanings as described above, and $R^5$ represents an optionally substituted alkyl group or optionally substituted phenyl group with a Grignard compound of the formula (5):

$R^2$—MgX (5)

wherein $R^2$ represents the same meanings as described above, and X represents a halogen atom, and wherein the optically active amino acid ester compound of the formula (4) is a compound obtained by treating an addition salt of the optically active amino acid ester compound and an acid with a tertiary amine compound base.

2. The production method according to claim 1, wherein the alcohol solvent is methanol.

3. The production method according to claim 1, wherein the copper compound is a divalent copper compound.

4. The production method according to claim 3, wherein the divalent copper compound is copper(II) acetate or copper (II) hydroxide.

5. The production method according to claim 3, wherein the divalent copper compound is copper(II) acetate.

6. The production method according to claim 1, wherein X in the formula (5) is a bromine atom.

7. The production method according to claim 1, wherein the tertiary amine compound is triethylamine.

8. A method of producing an asymmetric copper complex crystal comprising reacting an optically active salicylidene amino alcohol compound of the formula (1):

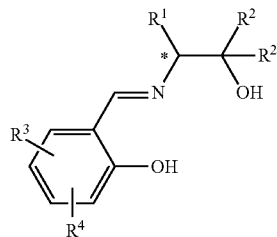
(1)

wherein, $R^1$ represents an alkyl group, aryl group or aralkyl group, $R^2$ represents an optionally substituted alkyl group or optionally substituted phenyl group, $R^3$ and $R^4$ are the same or mutually different and represent a hydrogen atom, halogen atom, nitro group, alkyl group, fluoroalkyl group, alkoxy group, alkoxycarbonyl group, trialkylsilyl group or cyano group, and * represents that the carbon atom is an optically active point with a copper compound, then, performing a crystallization treatment in the presence of an alcohol solvent, wherein the optically active salicylidene amino alcohol compound of the formula (1) is a compound obtained by reacting an optically active amino alcohol compound of the formula (2):

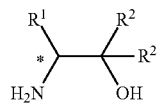
(2)

with a salicylaldehyde compound of the formula (3):

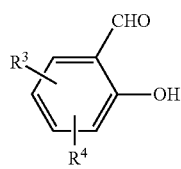
(3)

wherein the optically active amino alcohol compound of the formula (2) is a compound obtained by reading an optically active amino acid ester compound of the formula (4):

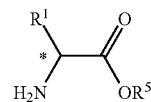
(4)

wherein, $R^1$ and * represent the same meanings as described above, and $R^5$ represents an optionally substituted alkyl group or optionally substituted phenyl group with a Grignard compound of the formula (5):

$$R^2-MgX \qquad (5)$$

wherein $R^2$ represents the same meanings as described above, and X represents a halogen atom, and wherein the optically active amino acid ester compound of the formula (4) is a compound obtained by treating an addition salt of the optically active amino acid ester compound and an organic sulfonic acid compound with a base.

9. The production method according to claim 8, wherein the organic sulfonic acid compound is p-toluenesulfonic acid.

10. The production method according to claim 1, wherein the temperature for treatment of an addition salt of the optically active amino acid ester compound of the formula (4) and an acid with a base is in the range of 0 to 10° C.

11. The production method according to claim 1, wherein $R^1$ in the formula (1) is an alkyl group having 1 to 4 carbon atoms.

12. The production method according to claim 1, wherein $R^1$ in the formula (1) is a methyl group.

13. The production method according to claim 1, wherein $R^2$ in the formula (1) is an optionally substituted phenyl group.

14. The production method according to claim 1, wherein $R^2$ in the formula (1) is a 2-n-butoxy-5-tert-butylphenyl group.

15. The production method according to claim 1, wherein $R^3$ is a hydrogen atom and $R^4$ is a nitro group in the formula (1).

16. The production method according to claim 15, wherein the nitro group represented by $R^4$ in the formula (1) is linked to the 5-position on the connected phenyl group.

* * * * *